United States Patent
Klipper

(10) Patent No.: US 12,201,623 B1
(45) Date of Patent: Jan. 21, 2025

(54) COMPOSITION AND METHOD FOR PREVENTING LONG-TERM COVID-19 MORBIDITY

(71) Applicant: Michael Klipper, Glen Head, NY (US)

(72) Inventor: Michael Klipper, Glen Head, NY (US)

(*) Notice: Subject to any disclaimer, the term of this patent is extended or adjusted under 35 U.S.C. 154(b) by 336 days.

(21) Appl. No.: 17/839,147

(22) Filed: Jun. 13, 2022

Related U.S. Application Data

(60) Provisional application No. 63/210,057, filed on Jun. 13, 2021, provisional application No. 63/209,960, filed on Jun. 11, 2021.

(51) Int. Cl.

| | | |
|---|---|---|
| *A61K 31/455* | (2006.01) |
| *A61K 9/14* | (2006.01) |
| *A61K 9/16* | (2006.01) |
| *A61K 9/48* | (2006.01) |
| *A61K 31/095* | (2006.01) |
| *A61K 31/315* | (2006.01) |
| *A61K 31/355* | (2006.01) |
| *A61K 31/375* | (2006.01) |
| *A61K 31/51* | (2006.01) |
| *A61K 31/593* | (2006.01) |
| *A61K 36/9066* | (2006.01) |
| *A61P 31/14* | (2006.01) |

(52) U.S. Cl.
CPC ............ *A61K 31/455* (2013.01); *A61K 9/145* (2013.01); *A61K 9/1617* (2013.01); *A61K 31/095* (2013.01); *A61K 31/315* (2013.01); *A61K 31/355* (2013.01); *A61K 31/375* (2013.01); *A61K 31/51* (2013.01); *A61K 31/593* (2013.01); *A61K 36/9066* (2013.01); *A61P 31/14* (2018.01); *A61K 9/4808* (2013.01)

(58) Field of Classification Search
CPC .... A61K 31/095; A61K 31/12; A61K 31/122; A61K 31/198; A61K 31/26; A61K 31/352; A61K 31/353; A61K 31/385; A61K 31/4415; A61K 31/4525; A61K 31/455; A61K 31/593; A61K 31/658; A61K 31/714; A61K 33/06; A61K 33/30; A61K 36/71; A61K 36/73; A61K 36/9066; A61K 38/06; A61K 38/4873
See application file for complete search history.

*Primary Examiner* — Savitha M Rao

(57) ABSTRACT

Disclosed is a pharmaceutical composition in one or more of a solid dosage form, a powder form, a liquid-filled capsule, and a softgel capsule for preventing long-term COVID-19 morbidity. The pharmaceutical composition includes a therapeutically effective amount of a mixture of: nicotinic acid, ascorbic acid, vitamin D, zinc picolinate, selenium, luteolin, methylcobalamin (B12), taurine, turmeric extract (>95% Curcumin), R-alpha-lipoic acid, d1-alpha-tocopheryl acetate (Vitamin E), Co-enzyme Q10 (CoQ10), acetyl-L-carnitine, pyrroloquinoline quinone (PQQ), 5-MTHF methyl folate, lutein, zeaxanthin, thiamine (B1), riboflavin (B2), biotin (B7), pyridoxine hydrochloride (B6), calcium ascorbate, magnesium bisglycinate, copper bisglycinate, panthothenate (B5), betain Hydrochloride, vitamin K2, and boron glycinate.

10 Claims, 1 Drawing Sheet

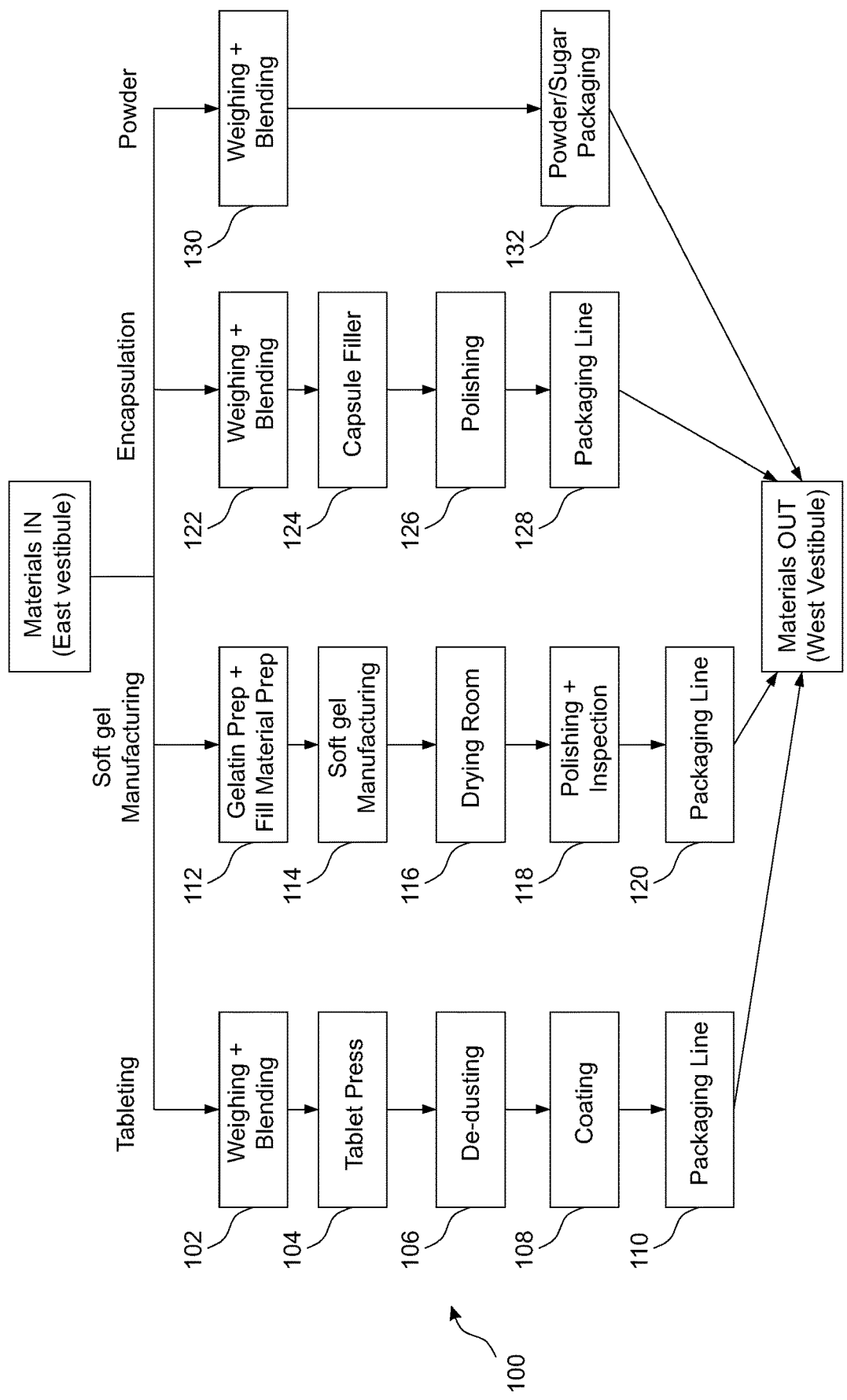

COMPOSITION AND METHOD FOR PREVENTING LONG-TERM COVID-19 MORBIDITY

CROSS-REFERENCE TO RELATED APPLICATIONS

This application claims priority to U.S. Provisional Patent Application No. 63/209,960 filed on Jun. 11, 2021 and U.S. Provisional Patent Application No. 63/210,057 filed on Jun. 13, 2021, the complete disclosures of which, in their entireties, are hereby incorporated by reference.

BACKGROUND

Technical Field

The inventive subject matter presented herein is generally directed towards a method and composition of preventing long-term COVID-19 morbidity. More particularly embodiments are related to a method and composition for preventing long-term COVID-19 morbidity by treating oxidative damage sequelae.

Description of the Related Art

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Typically, Coronaviruses are large, enveloped, single-strand RNA viruses that cause respiratory and/or enteric disease in mammals. COVID-19 disease is morbidity involving the SARS-COV-2 virus and the resulting hyper-oxidative/hyper-inflammatory state which often involves long-term morbidity in a large cross-section of individuals who have recovered from the acute stage. COVID-19 involves systematic oxidation and dysbiosis leading to the generation of auto-immune conditions, secondary infections of viral, bacterial, and fungal pathogens, neurological sequelae, and non-specific organ dysfunction.

US patent application US20200179367 filed by Williams Jonnie R. et al. discloses a coronavirus is treated by administering a pharmaceutical composition containing a therapeutically effective amount of isomyosmine or a pharmaceutically acceptable salt thereof. In another aspect, oxidative stress is reduced in an individual suffering from a coronavirus by administering a pharmaceutical composition containing a therapeutically effective amount of isomyosmine or a pharmaceutically acceptable salt thereof. In another aspect, mitochondrial reactive oxygen species (mtROS) are inhibited in an individual suffering from a coronavirus by administering a pharmaceutical composition containing a therapeutically effective amount of isomyosmine or a pharmaceutically acceptable salt thereof.

However, the existing methods and compositions focus on the cytokine response due to deregulation of the innate and adaptive immune system and are insufficient to prevent a variety of long-term morbidity. Currently, there are no promoted treatments that deal with the varied sequelae of systematic oxidative stress.

This specification recognizes that there is a need for a method and composition for preventing long-term COVID-19 morbidity by treating oxidative damage sequelae.

Further limitations and disadvantages of conventional and traditional approaches will become apparent to one of ordinary skill in the art through comparison of described systems with some aspects of the present disclosure, as set forth in the remainder of the present application and with reference to the drawings.

SUMMARY

A method and composition of preventing long-term COVID-19 morbidity by treating oxidative damage sequelae are provided and shown in and/or described in connection with the figures.

One aspect of the inventive subject matter relates to a pharmaceutical composition in one or more of a solid dosage form, a powder form, a liquid-filled capsule, and a softgel capsule for preventing long-term COVID-19 morbidity. The pharmaceutical composition includes a therapeutically effective amount of a mixture of: nicotinic acid, ascorbic acid, vitamin D, zinc picolinate, selenium, luteolin, methylcobalamin (B12), taurine, turmeric extract (>95% Curcumin), R-alpha-lipoic acid, d1-alpha-tocopheryl acetate (Vitamin E), Co-enzyme Q10 (CoQ10), acetyl-L-carnitine, pyrroloquinoline quinone (PQQ), 5-MTHF methyl folate, lutein, zeaxanthin, thiamine (B1), riboflavin (B2), biotin (B7), pyridoxine hydrochloride (B6), calcium ascorbate, magnesium bisglycinate, copper bisglycinate, panthothenate (B5), betain Hydrochloride, vitamin K2, and boron glycinate.

An aspect of the present disclosure relates to a pharmaceutical composition in one or more of a solid dosage form, a powder form, a liquid-filled capsule, and a softgel capsule for preventing long-term COVID-19 morbidity. The pharmaceutical composition includes a mixture of: a plurality of anti-oxidants; a plurality of Nicotinamide adenine dinucleotide (NAD+) supportive agents; a plurality of mitochondrial membrane supportive agents; nicotinic acid; a plurality of supplement co-factors; phospholipids; a plurality of vitamin B co-factors; a plurality of mitochondrial membrane building blocks; a plurality of mitochondrial membrane protective compounds, and curcumin.

An aspect of the present disclosure relates to a method of producing a pharmaceutical composition in one or more of a solid dosage form, a liquid-filled capsule, and a softgel capsule for preventing long-term COVID-19 morbidity. In operation, the processing of active and therapeutic ingredients for the present pharmaceutical composition (formula) begins with the weigh-out procedure, in which exact amounts of each active and therapeutic ingredient are weighed and verified using calibrated instruments. Each active and therapeutic ingredient is then evaluated for multiple quality variables including but not limited to moisture content, bulk and tapped densities, particle size, and surface adhesion. As these variables are measured, certain active ingredients may be milled and/or screened to increase the surface area of the particles. These particularly detailed actions are extraordinary and complementary to the further downstream process of blending, as it has a proprietary effect on the absorption and bioavailability of certain ingredients or combinations of ingredients. The manipulation of said quality variables allows and enhances surface-to-surface contact of these certain ingredients or combinations of ingredients in a manner that enhances and encourages larger quantities to pass through the digestive tract of the human body and enter the bloodstream, thus increasing the millimolarity concentration in the blood.

The processing step of blending for the 'formula' ingredients is then separated into unique categories of actives to have surface-to-surface contact and interactions, which form unions at the molecular level. Such unions are created by the unusual design and approach of contact and proprietary to the patent. These unions are complementary to how the human body's digestive tract identifies and absorbs such ingredients, whereas the digestive tract permits larger quantities to pass through absorption portals due to the blending technique executed. The pairing of actives for surface-to-surface contact is decided by comparing the vitamins, minerals, and other molecules of the formula to research and studies which have published their findings of enhanced absorption. General examples would be pairing Vitamin C+Iron, Vitamin B12+Folate, or Vitamin D+Calcium (see attachment). The proprietary blending technique has similarities to the design and premise of homeopathic medicine in that particular ingredients have physical contact with rigorous mixing (successions). In effect, the surface-to-surface contact with proper particle size, moisture content, aligned density, nutrient pairing, etc. allows for a unique and proprietary blending technique that enhances absorption in the digestive tract of human beings.

Accordingly, one advantage of the present inventive subject matter is that it involves the treatment of COVID-19 long-term morbidity with a nutraceutical composition. Specifically, the treatment of COVID-19 morbidity using a natural product's composition comprising a mixture of product classes specifically addressing the variety of biochemical dysfunction, specifically after the acute COVID-19 disease state, also known as "Long Covid", "Covid Long Haul", and "Post COVID 19 Syndrome".

According to an embodiment herein, the present disclosure provides a method and pharmaceutical/nutraceutical composition for preventing long-term COVID-19 morbidities by treating oxidative damage sequelae. The nutraceutical composition is used for the treatment of COVID-19 long-term morbidity. The natural product composition is used which includes a variety of biological dysfunctions. NAD+ (Nicotinamide adenine dinucleotide Chemical compound) supportive agents and mitochondrial membrane supportive agents are used for treating Oxidative damage sequelae to mitigate COVID-19 morbidity. The anti-oxidants are the main and most direct therapeutic mechanism for treating COVID-19 sequelae. The anti-oxidants directly block the effects of oxidation mechanisms. The DNA damage seen in COVID-19 indicates strong over-activation of PARP (Poly adenosine diphosphate-ribose polymerase) enzyme. Due to PARP over-activation, NAD+ is depleted and nicotinic acid is used as a therapeutic mechanism to replete NAD+. COVID-19 recovery involves the treatment of systematic oxidative damage by a number of co-factors. Zinc and selenium co-factors are required for DNA repair and B vitamin co-factors are required for proper mitochondrial function and repair. An amino acid supplement is also used and is an important part of COVID-19 recovery.

These features and advantages of the present disclosure may be appreciated by reviewing the following description of the present disclosure, along with the accompanying figures wherein like reference numerals refer to like parts.

BRIEF DESCRIPTION OF THE DRAWINGS

The accompanying drawings illustrate the embodiments of systems, methods, and other aspects of the disclosure. A person with ordinary skills in the art will appreciate that the illustrated element boundaries (e.g., boxes, groups of boxes, or other shapes) in the figures represent an example of the boundaries of such elements. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which:

FIG. 1 illustrates a flowchart of a method for producing a pharmaceutical composition in a tablet form, a softgel capsule form, an encapsulation form, and a powder form, in accordance with an embodiment of the present invention.

DETAILED DESCRIPTION

The present disclosure is best understood with reference to the detailed figures and description set forth herein. Various embodiments of the present systems and methods have been discussed with reference to the figures. However, those skilled in the art will readily appreciate that the detailed description provided herein including the figures are presented for explanatory purposes and the embodiments extend beyond the currently described embodiments. For instance, the teachings and results presented in any particular described application may yield multiple alternative approaches and may be implemented in any suitable manner.

The described embodiments may be implemented manually, automatically, and/or a combination of thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the embodiments pertains. Persons skilled in the art will envision many other possible variations that are within the scope of the claimed subject matter.

COVID-19 is a disease of systematic oxidation; this is clear due to the biomarkers that correlate with COVID-19 mortality and the expected biomarkers of oxidative stress. Studies have shown that RNA and DNA oxidative biomarkers are found in COVID-19 disease and free DNA may itself contribute to the inflammatory condition.

Free DNA from the mitochondria correlates and can predict the severity of COVID-19 disease, indicating oxidative damage as a driving mechanism of morbidity.

The use of anti-oxidants will significantly lower morbidity due to direct blocking effects on oxidation mechanisms, Vitamin C (ascorbate) is a preferential therapeutic due to its high bio-availability, inclusion in traditional diets, and fact that it is an endogenous molecule, furthermore, Ascorbate levels are shown to be low in COVID-19 hospitalized patients.

Anti-oxidants are the main and most direct therapeutic mechanism for treating COVID-19 sequelae, specifically when pro-inflammatory oxidative end-state compounds are present in the body.

Nicotinic acid, for a few reasons, is one of the main preferential therapeutic concepts for COVID-19. Network pharmacology and bioinformatics have identified nicotinic acid as one of the more relevant therapeutics, with a high safety margin.

In a recent review of COVID-19, niacin was mentioned as a therapeutic concept due to mechanistic understanding.

Furthermore, the DNA damage seen in COVID-19 indicates strong over-activation of PARP enzyme, Poly (ADP-ribose) polymerase is activated to repair double-strand DNA breaks caused by COVID-19 oxidative stress.

Due to PARP over-activation, NAD+ is depleted, nicotinic acid being the preferred therapeutic mechanism to replete NAD+.

Due to COVID-19 recovery involving the treatment of systematic oxidative damage, a number of co-factors are required, specifically co-factors for DNA repair and mitochondrial functioning. Zinc and Selenium are required for DNA repair methods. A number of B vitamins are required for proper mitochondrial functioning and repair, According to the book, Mitochondrial Medicine, "Biosynthesis of the component of the mitochondrial respiratory chain, coenzyme Q, is dependent on vitamins B2, B6, B12, folic acid, pantothenic acid, niacinamide, and vitamin C. Vitamins B1, B2, B6, niacin, biotin, folic acid, and pantothenic acid are important for metabolic pathways in mitochondrial respiration and energy production. Vitamins C, E, niacin, and folic acid belong to effective scavengers of free radicals; prevent mitochondrial oxidants formation and mitochondrial aging."

During systematic oxidative damage, the mitochondria are the main source of oxidative stress and when they are improperly supported, there is potential for a bioenergetic breakdown of the mitochondrial membranes, leading to a bioenergetically triggered oxidative stress cascade. An NIH review of supplements for primary mitochondrial disorders indicates compounds like ALA, CoQ10, Carnitine, and NAC as well as amino acids, vitamins, and flavonoids are clinically useful in supporting bioenergetic functioning.

During systematic oxidative damage, mitochondrial membranes and other cell membranes are damaged by reactive oxygen species and form lipid rafts, protein-lipid complexes, and other stable oxidative end products that will lead to a lack of bioenergetic functioning. To treat this oxidative damage triggered state, a method called "lipid replacement therapy" is utilized. Lipid Replacement Therapy involves the supplementation of phospholipids and other structural components which lead to a replacement of cellular and mitochondrial membranes, correcting bioenergetic functioning. Sunflower lecithin contains the required phospholipids and is a safe, sustainable source.

During systematic oxidative damage, proteins are an important target of reactive oxidative species, and the synthesis of proteins requires amino acid precursors. Furthermore, amino acids may directly act as therapeutics, such as the use of taurine in combination with niacin for treating oxidative-based lung fibrosis. Essential amino acids are 9 amino acids required for the human body to function properly and are available commercially as supplements, on-top of this, there are 8 amino acids that are "conditional" or only required after a disease or systematic insult. Amino acids may directly act on and modulate oxidative stress and any deficiencies may not only affect protein repair but also oxidative quenching leading to mortality. The use of an amino acid supplement that contains not only essential amino acids but also conditional amino acids is an important part of COVID-19 recovery. Flavonoids such as quercetin and lutein may serve a number of purposes, including stabilizing mast cells, lowering inflammation, and supporting antioxidant mechanisms through secondary means.

The following table 1 depicts various oxidative damage targets, long-term sequelae, and example treatments.

TABLE 1

| Oxidative Damage Targets | Long Term Sequelae | Example Treatments |
|---|---|---|
| DNA | NAD+ Depletion | Nicotinic acid |
| Proteins | Stabilized Oxidized Protein | Amino Acids |
| Lipids | Stabilized Oxidized Lipids | Lipid Replacement |
| Mitochondria | Bioenergetic Dysfunction | Membrane support |

In general, the invention relates to the treatment of COVID-19 long-term morbidity with a nutraceutical composition. Specifically, the treatment of COVID-19 morbidity using a natural product composition comprising a mixture of product classes specifically addressing the variety of biochemical dysfunction, specifically after the acute COVID-19 disease state. The systematic long term oxidative challenge will create a number of biochemical end states, including depletion of bioenergetic molecules such as NAD+, stable and oxidized lipids, and proteins, specifically in mitochondrial and other membranes and COVID-19 involves systematic oxidation, a review, "COVID-19 and Oxidative Stress" gives a number of the rationale for the use of anti-oxidants in the treatment of COVID-19 morbidity. The previously mentioned publication states: "Most notably, use of antioxidants seems reasonable at the stage requiring inhibition of inflammatory reactions during COVID-19. It is expected that such therapy may prevent organ and tissue damage due to cytokine storms and oxidative stress. Furthermore, lowering oxidative stress by antioxidants may result in a decreased viral load. A recent study with peripheral blood monocytes purified from the healthy volunteers demonstrated that SARS-COV-2 replication was suppressed by NAC and mitochondria-targeted antioxidant MitoQ allowing us to assume that the decreased ROS levels prevent HIF1-α activation and subsequent metabolic switch to glycolysis necessary for coronavirus replication. However, this hypothesis requires further investigation."

In one embodiment, the composition can include a mixture of anti-oxidants, nicotinic acid, mitochondrial support agents, and supplement co-factors, wherein the anti-oxidants is at least one of vitamin C, vitamin E or astaxanthin. More specifically a daily dosage of vitamin C between 200 mg-4000 mg, a daily dosage of vitamin E between 400 IU to 10,000 IU, and a daily dosage of astaxanthin between 2 mg to 20 mg. Most specifically a composition including a daily dosage of vitamin C of 800 mg and vitamin E daily dosage of 4000 IU.

COVID-19 affects bioenergetics of the body, most likely through the oxidative depletion of NAD+ due to DNA breaks causing over-activation of PARP. The publication, "Influence of NAD+ as an aging-related immunomodulator on COVID-19 infection: A hypothesis" states, "Elderly COVID-19 patients are at a real risk of complications due to impaired immune function, cytokine storm, and defective respiratory function. Administration of anti-aging immunomodulation factors like Nicotinamide Adenine Dinucleotide NAD+ can minimize these changes through its potent immunomodulation and longevity effects. NAD+ has a direct inhibitory effect on PARP-1 and can prevent pro-inflammatory cytokines over-activation. Increasing the NAD+ level will also result in stabilizing telomeres and this has a positive impact on immune cells function." There are a number of nutraceuticals that can increase the level of NAD+ including vitamin B3, resveratrol, Nicotinamide Mononucleotide, Nicotinamide riboside, pro-drug of nicotinic acid such as inositol hexanicotinate, or directly with NAD+. In the preferred embodiment, the NAD+ increasing agent is nicotinic acid in a daily dosage between 50 mg to 2000 mg, most specifically 240 mg daily dose.

The oxidative stress caused by COVID-19 involves the mitochondria, which are the main source of reactive oxidative species in the body in a number of disease states. In the research paper, "Circulating mitochondrial DNA is an early indicator of severe illness and mortality from COVID-19", it is stated that mitochondrial breakdown proxy biomarkers are highly correlated with long-term morbidity due to COVID-19. The research paper, "Mitochondrial dysfunction and oxidative stress in metabolic disorders-A step towards mitochondria based therapeutic strategies", shows the strong coupling of mitochondria and oxidative stress. This article states, "Mitochondria continuously function to metabolize oxygen and generate ROS. However, either by accident or for a purpose, the flow of electrons through the ETC is an imperfect process in which 0.4 to 4% of oxygen consumed by mitochondria is incompletely reduced and leads to the production of ROS such as superoxide anion (radical dotO2−) designated as "primary" ROS. Excessive generation of superoxide anion further interacts with many other compounds and generates "secondary" ROS. It is earlier established that the interactions of hydroxyl radical (radical dotOH) with DNA molecule damages the nitrogenous bases, purine and pyrimidine, and deoxyribose backbone of DNA. Also, the overproduction of ROS damages the mitochondrial proteins/enzymes, membranes, and DNA; which leads to the interruption of ATP generation and other essential functions in mitochondria. Besides superoxide anion and hydroxyl radicals, the ETC also generates other reactive species such as nitric oxide (NO) and reactive nitrogen species (RNS). Most of the cellular proteins and glutathione are affected through nitration induced by RNS. Free radicals are fundamental to any biochemical process and are continuously produced in the body. The cells have many ways to counter the effects of oxidative damage induced by ROS, either by directly diminishing the generation of free radicals or by scavenging the free radicals by an array of antioxidants, both enzymatic and non-enzymatic mechanisms."

In supporting the mitochondrial functioning after the oxidative assault of COVID-19 there are two main mechanisms, specifically supporting mitochondrial function and providing mitochondrial membrane building block compounds.

In the preferred embodiment of the invention, said mitochondrial function supporting agents include at least one of alpha-lipoic acid, coenzyme Q10 (ubiquinol), acetyl-carnitine, N-acetyl Choline, Resveratrol, and PQQ. Most specifically mitochondrial function supporting agents include at least one of alpha-lipoic acid at a daily dosage between 200 mg to 1200 mg, fully depleted coenzyme Q10 (ubiquinol) at a daily dosage between 20 mg to 500 mg, and acetyl-carnitine at a daily dosage between 200 mg and 2000 mg. In the preferred embodiment of the invention, said mitochondrial membrane building block agents include at least one of phospholipids, omega 3, omega 6, and wheat germ oil. Most specifically, a daily dosage of phospholipids between 2000 mg-10,000 mg, a ratio of omega-3 and omega-6 of 1:4.

In supporting the mitochondrial functioning after the oxidative assault of COVID-19 the depletion of specific vitamins may prevent proper functioning. Utilizing vitamins involved in bioenergetic functioning in a supplement treating COVID19, will prevent rate and substrate limited repair function. According to the book, "Mitochondrial Medicine", a number of vitamins, usually B vitamins, are involved in proper mitochondrial functioning. The book states, "Vitamins are essential in metabolic reactions in the body as catalysts in enzymatic reactions or as coenzymes carrying chemical groups between enzymes. Many vitamins function in enzyme complexes participating in mitochondrial respiration and energy production or they are required for the synthesis of mitochondrial respiratory chain components. Biosynthesis of the component of the mitochondrial respiratory chain, coenzyme Q, is dependent on vitamins B2, B6, B12, folic acid, pantothenic acid, niacinamide, and vitamin C. Vitamins B1, B2, B6, niacin, biotin, folic acid, and pantothenic acid are important for metabolic pathways in mitochondrial respiration and energy production. Vitamins C, E, niacin, and folic acid belong to effective scavengers of free radicals; prevent mitochondrial oxidants formation and mitochondrial aging. Some mitochondrial diseases are linked to vitamin deficiencies and can be improved by vitamin supplementation."

In the preferred embodiment of the invention, said mitochondrial support vitamins contain one or more of: methylcobalamin (B12), thiamine (B1), riboflavin (B2), biotin (B7), pyridoxine·hcl (B6), panthothenate (B5), calcium, magnesium, and copper. Most specifically the embodiment of the invention contains methylcobalamin in a daily dose between 0.05 mg to 0.5 mg, thiamine in a daily dose between 10 mg to 50 mg, riboflavin in a daily dose between 15-50 mg, biotin in a daily dose between 0.05 mg to 0.5 mg, pyridoxine in a daily dose between 15-50 mg and panthothenate in a daily dose between 2 mg to 10 mg.

In supporting of recovery of the systematic oxidative stress caused by COVID19, there are a number of other supplements addressing oxidative sequelae. Flavanoids and flavonols such as quercetin and luteolin may stabilize mast cells, have direct anti-viral activity, and lower inflammation, curcumin also has a number of these same mechanisms as well as iron scavenging abilities. Iron scavenging is important as there are no efficient iron scavenging mechanisms in the human body and COVID19 involves dramatic iron dysbiosis. Free iron will dramatically contribute to metal-catalyzed auto-oxidation and curcumin is, therefore, an important therapeutic concept. The paper, "Anemia and iron metabolism in COVID-19: a systematic review and meta-analysis" states, "Increased intracellular iron sequestration will lead to an upregulation of cytosolic ferritin, which sequesters and stores iron to prevent iron-mediated free radical damage. The increased retention and storage of iron within ferritin in macrophages contribute to the characteristic fall in serum iron concentrations and an increase in serum ferritin concentrations as observed in acute phase response. The net result will be diminished iron availability for erythropoiesis and as a result further aggravation of anemia. This is in line with our findings showing the worst erythrocyte phenotypes in severe COVID-19 patients compared to non-severe cases".

In the preferred embodiment of the invention, additional components include flavonoids such as quercetin, luteolin, and curcumin. More specifically the preferred embodiment of the invention includes one of, quercetin at a daily dose between 200 mg to 800 mg, a daily dose of luteolin between 50 mg to 400 mg, and a daily dose of curcumin between 200 mg to 2000 mg.

According to an embodiment herein, the present specification describes a pharmaceutical composition in solid dosage form for preventing long-term COVID-19 morbidity. As used herein, the term "pharmaceutical" may refer to a U.S. Federal Drug Administration (FDA) approved or non-FDA approved pharmaceutical composition. However, the enablement of the embodiments herein is not dependent on the approval/rejection of the FDA. The pharmaceutical composition includes a therapeutically effective amount of a mixture of: nicotinic acid, ascorbic acid, vitamin D, zinc picolinate, selenium, luteolin, methylcobalamin (B12), taurine, turmeric extract (>95% Curcumin), R-alpha-lipoic acid, dl-alpha-tocopheryl acetate (Vitamin E), Co-enzyme Q10 (CoQ10), acetyl-L-carnitine, pyrroloquinoline quinone (PQQ), 5-MTHF methyl folate, lutein, zeaxanthin, thiamine (B1), riboflavin (B2), biotin (B7), pyridoxine hydrochloride (B6), calcium ascorbate, magnesium bisglycinate, copper bisglycinate, panthothenate (B5), betain Hydrochloride, vitamin K2, and boron glycinate.

In an embodiment, the therapeutically effective amount of the nicotinic acid is at least 240 mg. In an embodiment, the therapeutically effective amount of the ascorbic acid is 930 mg. In an embodiment, the therapeutically effective amount of vitamin D is 0.125 mg. In an embodiment, the therapeutically effective amount of zinc picolinate is 25 mg. In an embodiment, the therapeutically effective amount of selenium is 0.2 mg. In an embodiment, the therapeutically effective amount of luteolin is 200 mg. In an embodiment, the therapeutically effective amount of the methylcobalamin (B12) is 0.1 mg. In an embodiment, the therapeutically effective amount of taurine is 600 mg. In an embodiment, the therapeutically effective amount of the turmeric extract (>95% Curcumin) is 500 mg. In an embodiment, the therapeutically effective amount of the R-alpha-lipoic acid is 150 mg. In an embodiment, the therapeutically effective amount of the dl-alpha-tocopheryl acetate (Vitamin E) is 25 mg. In an embodiment, the therapeutically effective amount of the Co-enzyme Q10 (CoQ10) is 100 mg. In an embodiment, the therapeutically effective amount of the acetyl-L-carnitine is 1500 mg.

In an embodiment, the therapeutically effective amount of the pyrroloquinoline quinone (PQQ) is 10 mg. In an embodiment, the therapeutically effective amount of the 5-MTHF methyl folate is 0.5 mg. In an embodiment, the therapeutically effective amount of lutein is 10 mg. In an embodiment, the therapeutically effective amount of zeaxanthin is 2 mg.

In an embodiment, the therapeutically effective amount of thiamine (B1) is 30 mg. In an embodiment, the therapeutically effective amount of riboflavin (B2) is 30 mg. In an embodiment, the therapeutically effective amount of the biotin (B7) is 0.1 mg. In an embodiment, the therapeutically effective amount of the pyridoxine Hydrochloride (B6) is 30 mg. In an embodiment, the therapeutically effective amount of the calcium ascorbate is 200 mg. In an embodiment, the therapeutically effective amount of the magnesium bisglycinate is 100 mg. In an embodiment, the therapeutically effective amount of the copper bisglycinate is 1 mg. In an embodiment, the therapeutically effective amount of the panthothenate (B5) is 5 mg. In an embodiment, the therapeutically effective amount of the betain Hydrochloride is 75 mg. In an aspect, the therapeutically effective amount of vitamin K2 is 0.2 mg. In an embodiment, the therapeutically effective amount of the boron glycinate is 5 mg. In an embodiment, the pharmaceutical composition prevents the long-term COVID19 morbidity by treating oxidative damage sequelae.

According to an embodiment herein, the present specification further describes a pharmaceutical composition in one or more of a solid dosage form, a powder form, a liquid-filled capsule, and a softgel capsule for preventing long-term COVID-19 morbidity. The pharmaceutical composition includes a mixture of: a plurality of anti-oxidants; a plurality of Nicotinamide adenine dinucleotide (NAD+) supportive agents; a plurality of mitochondrial membrane supportive agents; nicotinic acid; a plurality of supplement co-factors; phospholipids; a plurality of vitamin B co-factors; a plurality of mitochondrial membrane building blocks; a plurality of mitochondrial membrane protective compounds, and curcumin.

In an embodiment, the anti-oxidants include one or more of Vitamin C, Vitamin E, and Astaxanthine. In an embodiment, the NAD+ supportive agents comprise vitamin B3, resveratrol, Nicotinamide Mononucleotide, Nicotinamide riboside, and pro-drug of nicotinic acid comprising inositol hexanicotinate or NAD+. In an embodiment, the mitochondrial supportive agents comprise Alpha-lipoic acid, Coenzyme Q10 (ubiquinol), acetyl-carnitine, N-acetyl Choline, Resveratrol, and PQQ. In an embodiment, the supplement cofactors comprise vitamin B, curcumin, selenium, flavonoids, flavanols, taurine, vitamin K2, boric acid, melatonin, betain, chelated calcium, chelated magnesium, and chelated copper. In an embodiment, the supplement co-factors comprise one or more of zinc, selenium, vitamin D, B vitamins, or flavonoids.

In an embodiment, the mitochondrial building block components comprise phospholipids, omega 3 fatty acids, omega 6 fatty acids, and wheat germ oil. In an embodiment, the mitochondrial membrane protective compounds comprise one or more of alpha-lipoic acid, Coenzyme Q10 (ubiquinol), acetyl-carnitine, N-acetyl Choline, or PQQ. In an embodiment, the pharmaceutical composition prevents the long-term COVID19 morbidity by treating oxidative damage sequelae. The oxidative damage sequelae are caused by one or more of SARS-COV-2, secondary infections, environmental conditions, or dysfunction of the innate or adaptive immune system.

FIG. 1 illustrates a flowchart 100 of a method for producing a pharmaceutical composition in a tablet form, a softgel capsule form, an encapsulation form, and a powder form, in accordance with an embodiment of the present invention. The method of producing pharmaceutical composition in the tablet form initiates with a step 102 of weighing and blending exact amounts of each active and therapeutic ingredient. Then the method includes step 104 of performing a tablet press on the weighed and the blended active and therapeutic ingredients to obtain the pharmaceutical composition in the tablet form. At step 106, de-dusting is performed on the obtained tablets. The method includes a step 108 of coating the tablets and then, at step 110, the coated tablets are transferred to the packaging line for packaging.

According to an embodiment herein, the pharmaceutical composition is produced in a liquid-filled capsule for oral administration. In another embodiment, the pharmaceutical composition is produced in a liquid and beverage-filled hard capsule. In another embodiment, the pharmaceutical composition may be produced in a syrup or fluid form for oral administration.

The method of producing pharmaceutical composition in the softgel capsule form initiates with a step 112 of preparing gelatin and fill material. Then the method includes a step 114 of initiating manufacturing of the softgel. A softgel consists of a gelatin-based shell surrounding a liquid fill. The shells are a combination of gelatin, water, opacifier, and plasticizers, such as glycerin or sorbitol. Typically, in the encapsulation process, two flat ribbons are manufactured and brought together on a twin set of rotating dies. At step 116, the obtained softgel capsule of the present pharmaceutical composition is kept in the drying room. The method includes a step 118 of polishing and inspecting the dried softgel capsule and then, at step 120, the polished softgel capsules are transferred to the packaging line for packaging.

The method of producing pharmaceutical composition in the encapsulation form initiates with a step 122 of weighing and blending exact amounts of each active and therapeutic ingredient. Then the method includes the step 124 of filing the weighed and the blended active and therapeutic ingredients into a capsule by using a capsule filler. Capsule filler is a type of machine used to fill empty capsules with pharmaceutical ingredients. At step 126, the capsules are polished and then, at step 128, the polished capsules are transferred to the packaging line for packaging.

The method of producing pharmaceutical composition in the powder form initiates with a step 130 of weighing and blending exact amounts of each active and therapeutic ingredient. Then the method includes the step 132 of packaging the weighed and the blended active and therapeutic ingredients in the powder/sugar form.

Example 1

Two compositions of tablets are prepared to provide treatment for long-term COVID-19 morbidity. The first composition of said tablets, defined as Phase 1, are prepared to provide anti-oxidants, nicotinic acid, mitochondrial membrane supportive agents, and supplement co-factors. The tablets include the nutraceutical ingredients in Table 2 in the mentioned ratios and absolute daily values. The second composition of said tablets, defined as Phase 2, are prepared to provide amino acids and phospholipids, the tablets include the nutraceutical ingredients in Table 3 in the mentioned ratios and absolute daily values.

The dosing protocol may be simple, or in the preferred embodiment of the invention, a phased approach to modulate the autophagy process. In an autophagy leveraging embodiment, Phase 1 tablets will be taken in the daily amounts and ratios listed in Table 2 for 3 weeks, dosing three days out of seven days of the week. In the 4th week, Phase 2 tablets will be taken in the daily amounts and ratios listed in Table 3 dosing every single day, while Phase one dosing is also increased to every single day. Autophagy is triggered by pulsing Phase 1 tablet dosing but will be inhibited due to a large amount of amino acids in Phase 2 tablets; therefore Phase 2 is not started until the 4th week. In one embodiment of the invention, Phase 2 daily amounts and ratios listed in Table 3 may also be provided in the form of a powder, powdered drink, or snack bar format.

TABLE 2

| Phase 1 | |
|---|---|
| Nicotinic acid | 240 mg |
| Ascorbic acid | 930 mg |
| Vitamin D | 0.125 mg |
| Zinc Picolinate | 25 mg |
| Selenium | 0.2 mg |
| Luteolin | 200 mg |
| methylcobalamin (B12) | 0.1 mg |
| Taurine | 600 mg |
| Turmeric Extract (>95% Curcumin) | 500 mg |
| R-Alpha Lipoic Acid | 150 mg |
| dl-alpha tocopheryl acetate (Vitamin E) | 25 mg |
| CoQ10 | 100 mg |

TABLE 2-continued

| Phase 1 | |
|---|---|
| Acetyl-1-carnitine | 1500 mg |
| PQQ | 10 mg |
| 5-MTHF Methyl Folate | 0.5 mg |
| Lutein | 10 mg |
| Zeaxanthin | 2 mg |
| Thiamine (B1) | 30 mg |
| Riboflavin (B2) | 30 mg |
| Biotin (B7) | 0.1 mg |
| Pyridoxine.hcl (B6) | 30 mg |
| Calcium Ascorbate | 200 mg |
| Magnesium Bisglycinate | 100 mg |
| Copper Bisglycinate | 1 mg |
| Panthothenate (B5) | 5 mg |
| Betain.Hcl | 75 mg |
| Vitamin K2 | 0.2 mg |
| Boron Glycinate | 5 mg |

TABLE 3

| Phase 2 | |
|---|---|
| histidine | 1000 mg |
| isoleucine | 1000 mg |
| leucine | 1000 mg |
| lysine | 1000 mg |
| methionine | 1000 mg |
| phenylalanine | 1000 mg |
| threonine | 1000 mg |
| valine | 1000 mg |
| arginine | 750 mg |
| cysteine | 1000 mg |
| glutamine | 1000 mg |
| L-tyrosine | 1000 mg |
| glycine | 1000 mg |
| ornithine | 1000 mg |
| proline | 1000 mg |
| serine. | 1000 mg |
| Sunflower Lecithin | 8000 mg |
| Omega 3 | 1000 mg |
| Omega 6 | 2000 mg |

The formulation provided by the embodiments herein can be made into the form of a capsule, tablet, softgel, syrup, powder, and/or beverage (such as a vitamin drink, etc.), as well as others suitable for delivery of the formulation. Moreover, the formulation provided by the embodiments herein may be in the form of a dietary supplement or nutraceutical, according to an example. Furthermore, the formulation provided by the embodiments herein may be in the form of a pharmaceutical drug, according to another example.

A person skilled in the art will understand that the pharmaceutical composition is described herein for illustrative purposes and should not be construed to limit the scope of the disclosure.

A person with ordinary skills in the art will appreciate that the method and composition have been illustrated and explained to serve as examples and should not be considered limiting in any manner. It will be further appreciated that the variants of the above-disclosed system elements, modules, and other features and functions, or alternatives thereof, may be combined to create other different apparatuses, systems, or applications.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method of preventing long-term COVID-19 morbidity in a subject by treating oxidative damage sequelae, by administering to the subject a pharmaceutical composition comprising a therapeutically effective amount of a mixture of: about 240 mg of nicotinic acid, about 930 mg of ascorbic acid, about 0.125 mg of vitamin D, about 25 mg of zinc picolinate, about 0.2 mg of selenium, about 200 mg of luteolin, about 0.1 mg methylcobalamin (B12), about 600 mg of taurine, about 500 mg of turmeric extract (>95% Curcumin), about 150 mg of R-alpha-lipoic acid, about 25 mg of d1-alpha-tocopheryl acetate (Vitamin E), about 100 mg of Co-enzyme Q10 (CoQ10), about 1500 mg of acetyl-L-carnitine, about 10 mg of pyrroloquinoline quinone (PQQ), about 0.5 mg of 5-MTHF methyl folate, about 10 mg of lutein, about 2 mg of zeaxanthin, about 30 mg of thiamine (B1), about 30 mg of riboflavin (B2), about 0.1 mg of biotin (B7), about 30 mg of pyridoxine hydrochloride (B6), about 200 mg of calcium ascorbate, about 100 mg of magnesium bisglycinate, about 1 mg of copper bisglycinate, about 5 mg of panthothenate (B5), about 75 mg of betain Hydrochloride, about 0.2 mg of vitamin K2, and about 5 mg of boron glycinate.

2. The method of claim 1, wherein the pharmaceutical composition is made into the form of a capsule, tablet, softgel, syrup, powder, and/or beverage, as well as others suitable for delivery of the formulation, wherein the formulation may be in the form of a dietary supplement or nutraceutical, wherein the formulation may be in the form of a pharmaceutical drug.

3. The method of claim 1 where in the composition further comprises a mixture of: a plurality of anti-oxidants; a plurality of Nicotinamide adenine dinucleotide (NAD+) supportive agents; a plurality of mitochondrial membrane supportive agents; nicotinic acid; a plurality of supplement co-factors; phospholipids; a plurality of vitamin B co-factors; a plurality of mitochondrial membrane building blocks; a plurality of mitochondrial membrane protective compounds, and curcumin.

4. The method of claim 3, wherein the anti-oxidants include one or more of Vitamin C, Vitamin E, and Astaxanthin and the NAD+ supportive agents comprise vitamin B3, resveratrol, Nicotinamide Mononucleotide, Nicotinamide riboside, and pro-drug of nicotinic acid comprising inositol hexanicotinate or NAD+.

5. The method of claim 3, wherein the mitochondrial supportive agents comprise Alpha-lipoic acid, Coenzyme Q10 (ubiquinol), acetyl-carnitine, N-acetyl Choline, Resveratrol, and PQQ.

6. The method of claim 3, wherein the supplement cofactors comprise vitamin B, curcumin, selenium, flavonoids, flavanols, taurine, vitamin K2, boric acid, melatonin, betain, chelated calcium, chelated magnesium, and chelated copper.

7. The method of claim 2, wherein the supplement co-factors comprise one or more of zinc, selenium, vitamin D, B vitamins, or flavonoids.

8. The method of claim 3, wherein the mitochondrial building block components comprise phospholipids, omega 3 fatty acids, omega 6 fatty acids, and wheat germ oil.

9. The method of claim 3, wherein the mitochondrial membrane protective compounds comprise one or more of alpha-lipoic acid, Coenzyme Q10 (ubiquinol), acetyl-carnitine, N-acetyl Choline, or PQQ.

10. The method of claim 1, wherein the oxidative damage sequelae are caused by one or more of SARS-COV-2, secondary infections, environmental conditions, or dysfunction of the innate or adaptive immune system.

* * * * *